United States Patent [19]

Vary

[11] Patent Number: 4,795,701

[45] Date of Patent: * Jan. 3, 1989

[54] HOMOGENEOUS POLYNUCLEOTIDE DISPLACEMENT ASSAY METHOD KIT AND REAGENT COMPLEX

[75] Inventor: Calvin P. H. Vary, Califon, N.J.

[73] Assignee: Allied Corporation, Morris Township, N.J.

[*] Notice: The portion of the term of this patent subsequent to Aug. 30, 2005 has been disclaimed.

[21] Appl. No.: 755,996

[22] Filed: Jul. 17, 1985

[51] Int. Cl.⁴ .......................... C12Q 1/68; C12Q 1/34; C12Q 1/42

[52] U.S. Cl. .......................................... 435/6; 435/4; 435/18; 435/19; 435/21; 435/810; 436/501; 536/26; 536/27; 536/28; 935/77; 935/78

[58] Field of Search ...................... 435/6, 7, 810, 4, 18, 435/19, 21; 436/501; 935/77, 78; 536/28, 26, 27

*Primary Examiner*—Robert J. Warden
*Assistant Examiner*—Jack Spiegel
*Attorney, Agent, or Firm*—Alan M. Doernberg

[57] ABSTRACT

An RNA signal strand is displaced from a probe strand by a target nucleotide sequence. Without separation, a digestion enzyme selective for displaced RNA, e.g., a polynucleotide phosphorylase, digests the displaced RNA to nucleoside phosphates including ADP. The digestion products are detected, e.g. by phosphorylating the ADP to ATP and detecting the ATP by bioluminescence.

31 Claims, 3 Drawing Sheets

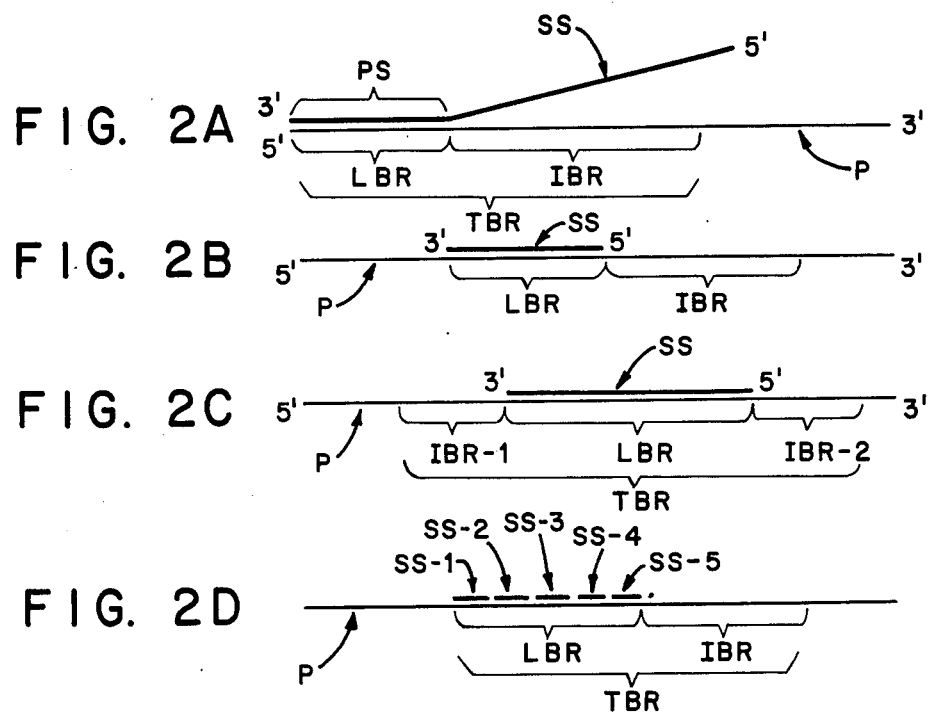
FIG. 2A
FIG. 2B
FIG. 2C
FIG. 2D
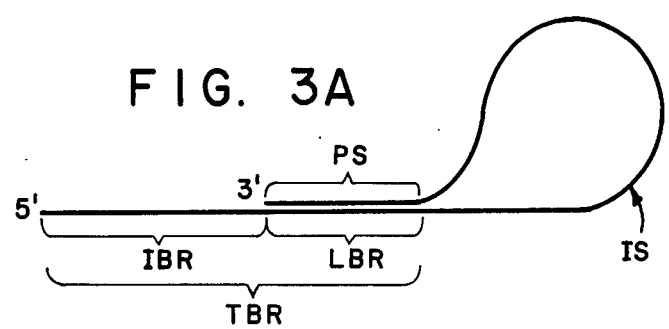
FIG. 3A
FIG. 3B
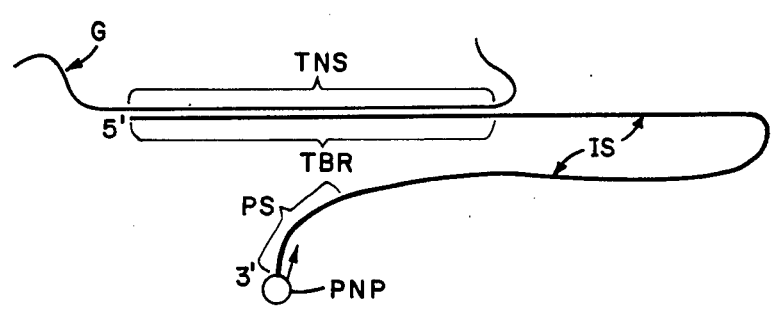

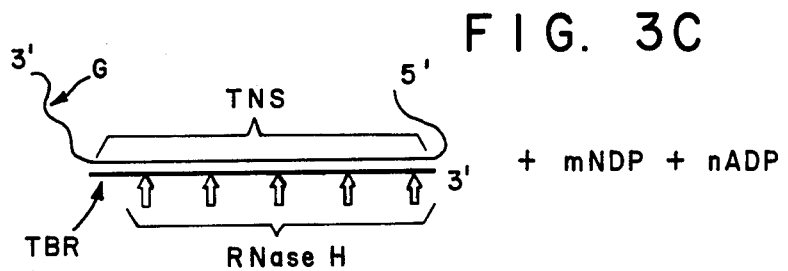
FIG. 3C
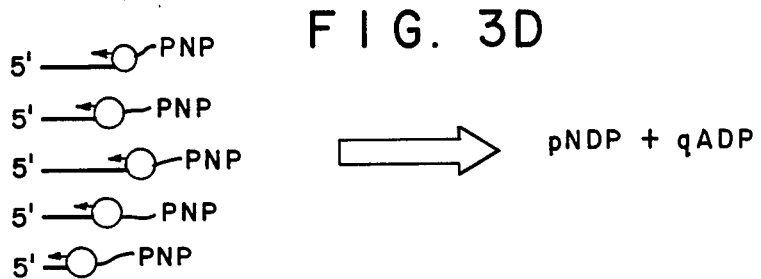
FIG. 3D
FIG. 3E
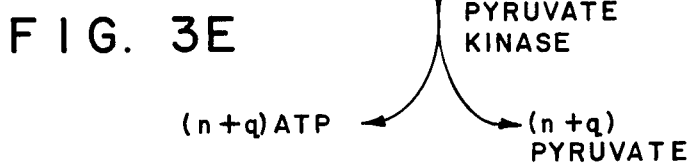
FIG. 4A
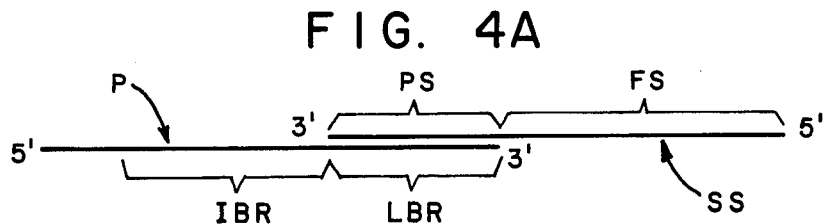
FIG. 4B
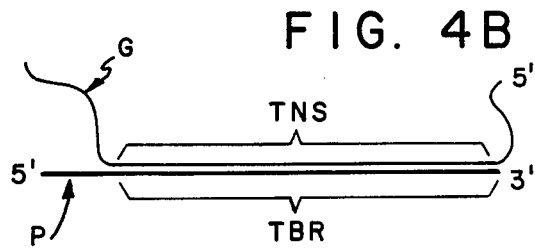

HOMOGENEOUS POLYNUCLEOTIDE DISPLACEMENT ASSAY METHOD KIT AND REAGENT COMPLEX

BACKGROUND OF THE INVENTION

The present invention relates to polynucleotide assays, especially for diagnostic purposes, and to kits and polynucleotide reagent complexes for such assays.

U.S. patent application Ser. No. 607,885 of S. E. Diamond et al, filed May 7, 1984 and assigned jointly to Allied Corporation and Genetics Institute, Inc., describes a polynucleotide displacement assay for target nucleotide sequences of sample nucleic acids. In such assays, a probe polynucleotide contains a segment (the target binding region) complementary to the target nucleotide sequence to be determined. A second polynucleotide, called the Labeled Polynucleotide or the Signal Strand, is bound by complementary base pairing to at least a portion of the target binding region. In use, such a reagent complex containing probe polynucleotide and signal strand is contacted by a sample; target nucleotide sequences in the sample bind to the target binding region of the probe polynucleotide and displace the signal strand from the reagent complex. Displaced signal strands are then detected, generally after a separation step which involves in many cases a probe polynucleotide which is either immobilized to a solid support before the sample is brought in or is immobilized to a solid support after the displacement step. Only limited embodiments are disclosed which can be conducted in a homogenous manner (without a separation step).

Such displacement assays have various advantages (as described in U.S. application Ser. No. 607,885) over prior hybridization assays represented by U.S. Pat. No. 4,358,535 to Fllkow et al (1982) in that difficulties associated with immobilizing the sample nucleic acid are eliminated. For most readouts (determinations of the displaced labeled polynucleotide or signal strand), however, a separation step is required.

Application U.S. Ser. No. 729,503 of C. Vary et al, filed May 2, 1985, describes a heterogenous assay of the displacement polynucleotide type wherein the displaced signal strand (labeled polynucleotide) has a digestable polyribonucleotide segment, especially at its 3' end. After displacement by target nucleotide strand and separation, such signal strands are digested (especially by the enzyme polynucleotide phosphorylase) to ribonucleoside phosphates (especially diphosphates) and the adenosine phosphates so produced (especially adenosine diphosphate) are determined. Such determination proceeds especially by phosphorylation to adenosine triphosphate (ATP) and determination of the ATP (e.g., with the luciferase catalyzed reaction with luciferin) or of the by-product of the phosphorylation step (e.g., pyruvate determination using NADH and lactate dehydrogenase). See also U.S. application Ser. No. 729,502 of C. Vary et al, filed May 2, 1985, for a further discussion of the digestion, phosphorylation and determination steps which may be used to assay displaced signal strands containing a digestable polyribonucleotide segment.

BRIEF DESCRIPTION OF THE INVENTION

Techniques have been discovered to conduct a displacement polynucleotide assay with digestion of the displaced signal strand and determination of adenosine phosphate digestion products operating in a homogeneous assay mode. Accordingly the present invention provides a method for determining the presence of a predetermined target nucleotide sequence in the DNA of a biological sample which comprises the steps:

(a) providing a reagent complex of (i) a probe polynucleotide which is capable of base pair binding via hydrogen bonds of purine/pyrimidine bases to the DNA target nucleotide sequence, and (ii) an RNA signal strand polynucleotide which is bound by base pair binding via hydrogen bonds of purine/pyrimidine base pairs to the probe polynucleotide in a region of the probe polynucleotide at least partially coextensive with the region in which the probe polynucleotide is capable of binding to the DNA target nucleotide sequence;

(b) contacting the reagent complex with a sample under conditions in which the DNA target nucleotide sequence, if present, binds to the probe polynucleotide and displaces the RNA signal strand polynucleotide from the reagent complex;

(c) without separation, digesting the displaced RNA signal strand polynucleotide selectively with respect to RNA signal strand polynucleotide remaining in reagent complex; and (d) detecting the presence of the digestion products of digesting the displaced RNA signal strand polynucleotide.

In preferred forms of such method, the signal strand contains a 3'-terminal ribonucleotide segment bound in the reagent complex to nucleotides of the target binding region, which cannot be digested so-bound by polynucleotide phosphorylase, but which after displacement are digested by polynucleotide phosphorylase to ribonucleoside diphosphates including adenosine diphosphate, which is determined.

The present invention also provides a kit for determining the presence of a predetermined target nucleotide sequence in the DNA of a biological sample which comprises:

(a) a reagent complex of (i) a probe polynucleotide which is capable of base pair binding via hydrogen bonds of purine/pyrimidine bases to the DNA target nucleotide sequence, and (ii) an RNA signal strand polynucleotide which is bound by base pair binding via hydrogen bonds of purine/pyrimidine base pairs to the probe polynucleotide in a region of the probe polynucleotide at least partially coextensive with the region in which the probe polynucleotide is capable of binding to the DNA target nucleotide sequence, the 3'-terminal nucleotide of the RNA signal strand polynucleotide being bound in the reagent complex to a nucleotide of the probe polynucleotide and the probe polynucleotide not containing an unbound 3'-terminal ribonucleotide having a 3' hydroxyl;

(b) a digestion enzyme specific for 3'-terminal ribonccleotides which are unbound;

(c) reactants and enzymes effective to convert adenosine phosphates produced by the digestion enzyme to ATP, and (d) means for detecting ATP or a byproduct of the conversion of adenosine phosphates to ATP.

The present invention further provides a reagent complex useful in such method and kit which comprises such a probe polynucleotide and such a RNA signal strand polynucleotide.

BRIEF DESCRIPTION OF THE DRAWING

FIG. 2A is a schematic view of a reagent complex according to a second embodiment of the present invention.

FIG. 2B is a schematic view of a reagent complex according to a third embodiment of the present invention.

FIG. 2C is a schematic view of a reagent complex according to a fourth embodiment of the present invention.

FIGS. 3A, 3B, 3C, 3D and 3E are schematic views of successive stages of a fifth embodiment of the present invention.

FIG. 4A is a schematic view of a reagent complex according to a sixth embodiment of the present invention.

FIG. 4B is a schematic view of the reagent complex of FIG. 4A after displacement of the signal strand (no longer shown).

DETAILED DESCRIPTION OF THE INVENTION

Figure 1A:
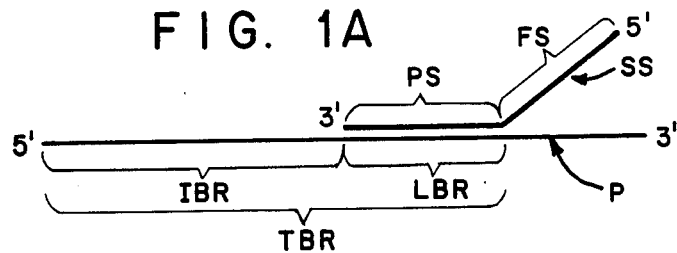
in FIG. 1A, the reagent complex.

The basic elements of the reagent complex provided by the present invention and used in the method and kit of the present invention are a probe polynucleotide and a signal strand, which as described below, may either be bound to each other only by complimentary base pairing or which may be further covalently attached by phosphate/sugar polynucleotide backbone (or otherwise be further attached covalently or non-covalently). The probe polynucleotide has a target binding region complementary to the target nucleotide sequence which will be determined. As described more fully in U.S. application Ser. No. 607,885, the target binding region may be perfectly complementary to the target nucleotide sequence or may contain a limited number of mismatches. Furthermore, the target binding region is conveniently divided into a portion called the Signal Strand Binding Region (or Labeled Polynucleotide Bindnng Region and thus LBR in the figures) to which a portion of the signal strand is bound by complimentary base pairing in the reagent complex. As illustrated by FIG. 1G of U.S. Ser. No. 607,885, a small number of additional bases of the signal strand may be bound to a small portion of the probe polynucleotide outside the target binding region (called the Residual Binding Region or RBR) but such residual binding region is preferably not present. A further portion (or portions) usually present in the target binding region of the probe polynucleotide is in single-stranded form in the reagent complex and is referred to as the initial binding region (IBR) in that the target nucleotide sequence can bind initially in this region prior to any displacement of nucleotides of the signal strand. As described in U.S. Ser. No. 607,885, the size of the target binding region is not independently critical, but can be thought as the sum of preferred or more preferred lengths of LB and IBR. The signal strand binding region (LBR) is preferably at least 25 nucleotides in length, more preferably 50–1000 nucleotides in length and most preferably 300–1000 nucleotides in length. The initial binding region is preferably at least 20 nucleotides in length, more preferably at least 500 nucleotides in length, and most preferably between about 500 and about 1000 nucleotides in length, inclusively. It is preferred that the signal strand binding region (LBR) be at or near an end of the target binding region (TBR) such that a single contiguous initial binding region (IBR) represents all or essentially all of the target binding region (TBR) not part of the signal strand binding region (LBR). As illustrated in FIG. 2C, below, however, the signal strand binding region (LBR) may be located other than at an end of the target binding region (TBR), in which case two initial binding regions (IBR-1) and (IBR-2) will be present.

The probe polynucleotide may be either DNA or RNA or may be a polynucleotide with both deoxyribonucleotides and ribonucleotides, especially in block copolymer structure. In the present invention, the target nucleotide sequence to be assayed is generally DNA and not RNA. If sample RNA were present, it could be pretreated (e.g., by derivatizing 3' ends) to make such sample RNA non-digestable in the later digestion steps of the invention. If the probe polynucleotide is DNA, as in many forms of the invention, there are no special constraints imposed upon the probe polynucleotide for the present invention compared to those described in U.S. application Ser. No. 607,885. If the probe polynucleotide is RNA or is a heteropolynucleotide containing ribonucleoiides, then the ribonucleotide segments of the probe polynucleotide should not be digestable by the digestion enzyme or method described below so long as the reagent complex remains intact. Using, for example, polynucleotide phosphorylase or other structure sensitive processive enzymes for this step, the probe polynucleotide should not contain a terminal 3' ribonucleotide segment unless such segment is bound by complimentary base pairing in the reagent complex (in which case it is preferably bound by complimentary base pairing to nucleotides of the signal strand as described belww and illustrated in FIGS. 3A and 4A).

The signal strand polynucleotide used in the method, kit and reagent complex of the present invention contains at least ribonucleotide segments, and is preferably RNA. An important feature of the present invention is that such nucleotide segments be digestable by the digestion enzyme or step described below once displaced from the probe polynucleotide, but not be digestable by such enzyme or step so long as the signal strand remains bound by complimentary base pairing to the probe polynucleotide. For simplicity, it is assumed first that the signal strand is entirely RNA. Embodiments wherein the signal strand also contains deoxyribonucleotides are readily apparent.

As in U.S. application Ser. No. 607,885, at least a portion of the signal strand is bound by complimentary base pairing to a portion of the probe polynucleotide at least partially coextensive with the target binding region (and preferably wholly contained within the target binding region). Such pairing should protect such segment and the entire signal strand from digestion. Thus, when the digestion is with a processive enzyme such as polynucleotide phosphorylase, such pairing should include the 3' end of the signal strand. Such pairing of the 3' end protects the entire signal strand against digestion by such a processive enzyme.

A non-processive digestion enzyme can be used, either alone or in combination with a processive digestion enzyme. If such enzyme can digest any single-stranded ribonucleotide segment, including such segments which are not at an end, then it will normally be required that the entire ribonucleotide portion of the signal strand be bound by complimentary base pairing in the reagent complex, and especially be bound to nucleotides of the probe polynucleotide. For embodiments with solely processive digestion enzymes, however, a portion, and suitably a large portion of the signal strand may be ribonucleotides in single-stranded form. Snnce the 3' end of the signal strand is bound, such signal stranded segment (or Free Segment) of the signal strand will normally be nearer to the head (i.e., near the 5' end) of the signal strand than the pairing segment (PS) which is bound by complimentary base pairing to the probe polynucleotide (See FIGS. 1A and 4A). Thus, in many embodiments of the invention, the probe polynucleotide P is DNA, the signal strand SS is RNA and the pairing segment (PS) of the signal strand is bound by complimentary base pairing to the signal strand binding region LBR which is a part of (and preferably at an end of) the target binding region TBR of the probe polynucleotide P.

In other forms of the invention, the probe polynucleotide is RNA which is protected in the reagent complex against digestion by the digestion enzyme or step described below. Considering, for example, the embodiments using a processive enzyme, the 3' end of the RNA probe polynucleotide should be blocked in the reagent complex. Some forms of blocking will continue to protect the probe polynucleotide from digestion by the processive enzyme even after displacement. Such forms include the use of a covalent circular, or 3' hairpin RNA probe polynucleotide (thus having no free 3' end), and RNA probe polynucleotides wherein the 3' end is derivatized either chemically (such as by phosphate addition to the terminal 3'-hydroxyl or oxidation by periodate followed by reduction with sodium borohydride), by elongation with deoxyribonucleotides at the 3' end or by attachment to a support. It is preferred, however, that the 3' end of the RNA probe polynucleotide be blocked in the reagent complex only by complimentary base pairing to the pairing segment of the signal strand. Thus, a separate RNA probe polynucleotide may be hybridized to a separate signal strand in a fashion wherein the 3' end of each is bound by complimentary base pairing to nucleotides of the other. Such a reagent complex is illustrated in FIG. 4A. Alternatively, the 3' end of the probe polynucleotide may be hybridized back upon itself in a loop, such that the signal strand and probe are part of a continuous polynucleotide, and especially a continuous RNA polynucleotide. Such a reagent complex is illustrated in FIG. 3A. In such an embodiment, the probe polynucleotide contains no 3' end, but rather, upon displacement of the pairing segment PS from the signal strand binding region LBR of the target binding region TBR, a processive enzyme may digest through the pairing segment, through the intermediate segment IS which can be considered as a part of either the signal strand or the probe polynucleotide or some of each, and then (in some cases) through the target binding region.

In the use of the reagent complex and kit of the present invention, and in accordance with the method of the present invention, a sample to be analyzed is concentrated and treated to convert such DNA into detectable form. It is first desirable to release the DNA from structures (cells, viruses) by sonication, extractions or other physical or chemical treatments, and then to concentrate the nucleic acid fraction. In some forms of the invention, the sample DNA may be cut randomly or at specified locations (e.g., by restriction enzymes) and/or denatured. Exemplarly treatments include denaturation with sodium dodecyl sulfate (SDS) or guanidinum thiocyanate, strong alkali treatment, proteolysis, RNAse treatment, phenol extraction or some combination of these. For the present invention, it is desirable to remove endogenous RNA, and may be desirable to remove endogenous ADP and ATP (and in some forms of the invention endogenous AMP). Endogenous RNA can be removed by alkaline conditions (e.g., NaOH), which also denatures the double-stranded DNA. Endogenous ATP, ADP and AMP can be consumed enzymatically (e.g., with phosphatases or pyrophosphatases which are inactivated and/or removed after this step) if desired. As described in U.S. Ser. No. 729,503, however, once endogenous RNA is removed, one can, in some forms of tne invention, deal with endogenous ATP, ADP and (in some forms) AMP as a known background value (and then deal with them mathematically), rather than to use chemical, biochemical or physical methods, as in other forms of the invention.

Base treatment is a particlarly preferred form of dealing with endogenous RNA because, even if the conversion to nucleosides is incomplete, the polyribonucleotides remaining will generally have 3'-terminal phosphates. PNP has very little activity to convert 3'-terminal phosphate containing polyribonucleotides to nucleoside diphosphates.

Of the extractions available, extractions with boronates are preferred, because they capture molecules with vicinal hydroxyls (as are present in RNA, in ribonucleosides and in ribonucleoside phosphates), but allow DNA to elute.

Once the sample is so prepared, it is mixed with the reagent complex of the present invention. Because no subsequent separation will be required, it is preferred that this mixing or contacting occur totally in solution, although in less preferred forms of the invention one or both of the sample nucleic acid and reagent complex is immobilized on a solid phase. The mechanism of nucleation (initial hybridization of the target nucleotide sequence of the sample nucleic acid to the target binding region of the probe polynucleotide) can be that described in U.S. application Ser. No. 607,885 or any of the mechanisms described in U.S. application Ser. No. 684,305 of M. Collins et al, filed Dec. 20, 1984 and copending. In the absence of the recombination proteins described in such application of Collins et al, nugleation will normally occur at the initial binding region IBR of the probe polynucleotide of the reagent complex. Such nucleation can be enhanced either by the volume-exclusion polymers of U.S. Ser. No. 684,308 of J. I. Williams, et al. (e.g., poly (ethylene oxide)), or by proteins of U.S. Ser. No. 684,305 of M. Collins, et al. or the DNA/DNA helix promoters discussed below (Netropsin or Distamycin A). If insufficient ATP is present during displacement for rec A protein to be effective, other proteins not dependant or ATP, e.g., Gene 32 protein (with polyamine cofactors) or E. coli single stranded binding protein, may still be useful. See S. C. Kowalczykowski, et al. in *The Enzymes*, vol. XIV, pp. 373–444 (1981). Furthermore, cascades are contemplated wherein ADP produced by subsequent digestion is phosphorylated to ATP, which activates rec A in promoting displacement with resultant ADP production (from the ATP hydrolyzed by rec A protein and from the ADP derived from the displaced strand).

Such nucleation at initial binding region IBR is then followed by migration of double strandedness between the target binding sequence and the probe polynucleotide into the signal strand binding region LBR. As described more fully in connection with 1A-1E of U.S. application Ser. No. 607,885, a microscopic phenomenon (described there as zipping/unzipping) may occur within the signal strand binding region LBR but, generally within a very short time period, the target nucleotide sequence will totally displace the pairing segment of the signal strand from the target binding region of the probe polynucleotide. At that point, if the signal strand is a separate polynucleotide from the probe polynucleotide, it will be released entirely from the probe polynucleotide. If, however, the probe polynucleotide and signal strand form a part of a continuous polynucleotide, the covalent attachment will remain, but the portion of the continuous strand which includes the signal strand will be transformed into totally single-stranded form.

In embodiments of the present invention wherein the probe polynucleotide is DNA and the signal strand pairing segment is RNA, it is contemplated to use additional agents during the displacement which favor the formation of a double helix between DNA and DNA (that is between the target nucleotide sequence and the probe polynucleotide) over a double helix between RNA and DNA. Such enhancers include Netropsin and Distamycin A. While such enhancers are particularly useful in the present invention and that of U.S. application Ser. No. 729,503, they may also be used for any displacement of an RNA signal strand or labeled polynucleotide from a DNA probe polynucleotide by a DNA competitor (sample) strand having the target nucleotide sequence.

The result of such displacement event is to release RNA signal stranded polynucleotides either into solution or to free their 3' ends (or otherwise render them digestable). They may now be digested and the adenosine phosphate digestion products determined as described below.

In some forms of the invention, however, the target binding region TBR of reagent complexes which have been subjected to displacement may also serve as a source for adenosine phosphates. After the displacement, it will be appreciated that such target binding region TBR is in a DNA/RNA (or A) double helical configuration with the DNA target nucleotide sequence. This applies of course only when the target binding region is a ribonucleotide segment and would not apply when the target binding region is a deoxyribonucleotide segment. The digestion of such RNA/DNA helices can proceed as follows. An enzyme with endonucleolytic ribonuclease H (RNase H) activity can be present or added to selectively digest RNA segments which are part of such a DNA/RNA or "A" form helix. Since this is an endonuclease, it will typically cut the RNA target binding region into a series of short ribonucleotides possessing free 3' hydroxyls (typically 6-10 nucleotides in length, such length being controlled by RNase H digestion parmmeters). Under appropriate conditions of temperature and concentration, these short ribonucleotides will spontaneously disassociate from the DNA target nucleotide sequence. Once such oligoribonucleotides are released, they become available for digestion as described below in the same manner as the displaced signal strand polynucleotides. Thus, if polynucleotide phosphorylase is to be used for the digestion step, it will processively digest both such freed oligoribonucleotides of the target binding region and the displaced signal strand polynucleotide to ribonucleoside phosphates. If the RNase H digestion is sufficient to permit all or substantially all of the target binding region nucleotides to disassociate from the target nucleotide sequence, then the target nucleotide sequence is now ready to nucleate to an initial binding region of another reagent complex molecule and repeat the displacement step. It is contemplated, however, that even if some small portion of the ribonucleotide target binding region remains attached to the DNA target nucleotide sequence, displacement may still be possible, in which case the displacement both displaces signal strand polynucleotide from the second reagent complex and displaces residual oligoribonucleotide pieces from the target nucleotide sequence.

The above-described use of RNase H activity to enhance the signal from the present displacement assay also has applicability to hybridization (not displacement) assays in which a probe RNA lacking a free 3' end is employed to form an "A" form helix with sample DNA. In such an assay, PNP-digestible RNA (having a free 3' end) is generated by RNase H cleavage if, and only if, probe/sample hybridization has occurred.

In the digestion step of the present invention, at least signal strand ribonucleotides (and, as described above also in some cases portions of the probe polynucleotide) are digested if and only if a displacement event has occured. Such digestion may be by enzymes such as E. coli RNAse II or rat liver alkaline RNase I, which attack any ribonucleoside segments which are single stranded and which convert such segments to ribonucleoside monophosphates including adenosine monophosphate (AMP) (this and all subsequent reference to ribonucleoside phosphate should be understood to mean the 5'-phosphate). It is preferred, however, to use an enzyme for the digestion step which proceeds processively from the 3' end (such as snake venom phosphodiesterase), and especially to use such processive enzymes which produce ribonucleoside diphosphates including adenosine diphosphate (ADP). Such processive adenosine diphosphate producing enzymes are generically known as polyribonucleotide phosphorylases (PNP) in that they transfer a phosphate moiety from inorganic phosphate in solution to each 3' end nucleotide so as to form the corresponding ribonucleoside diphosphate. Such enzymes generally remain attached to the 3' end of the ribonucleotide segment and generally will only attack ribonucleotide segments whose 3' ends have a terminal OH and are in single-stranded form. It is not, however, required that the polyribonucleotide segment to be digested be entirely in single-stranded form, provided that any double-strandedness present (and especially internal pairing) be sufficiently short to form and disassociate at sufficient frequency for the polynucleotide phosphorylase to proceed through such segments when they are in a single-stranded form.

In some preferred forms of the invention where the predominant digestion enzyme is processive (e.g., PNP or SVP) another digestion enzyme may also be present. Such other digestion enzyme is in some forms selective for short RNA/RNA double helical segments such as may be formed by internal pairing of the displaced signal strand segment: examples include cobra venom RNase, rat liver alkaline RNAse I and E. coli. RNAse II. Such auxiliary digestion enzymes should leave terminal 3' hydroxide for subsequent attack by the processive enzymes and, preferably, not cleave at bonds at the 5' carbon of adenosines (both conditions being met for cobra venom RNase). Such auxiliary digestion enzymes are generally used only where the target binding region is DNA, since otherwise the secondary enzyme will cleave RNA/RNA segments of intact reagent complexes, generating a false signal.

If a processive enzyme were available selective for free 5' ends, then a reagent complex could be constructed with a signal strand polyribonucleotide segment having its 5'-terminal nucleotide bound by complementary base pairing to the target binding region of the probe. The kit and method would correspond to those described above with appropriate changes of 3' ends for 5' ends. A candidate enzyme for such a kit is *E. Coli* RNAse V, which requires procaryotic protein biosynthetic enzymes for activity, but digests RNA processively from the 5' end to the 3' end.

Once ADP (or in some cases, AMP) is formed by such a digestion step, it is phosphorylated to ATP, preferably by an enzymatic reaction such as that of pyruvate kinase or creatine kinase, with the appropriate high energy phosphate cofactor (organophosphate) for such reaction (phosphoenolpyruvate and creatine phosphate, respectively). Detection thereafter of the ATP, or of the byproduct (e.g., pyruvate) can be as described in U.S. application Ser. Nos. 729,502 and 729,503.

As described more fully in those applications, it is preferred that the enzymes and organophosphate for such phosphorylation be present during the digestion with PNP so as to drive the otherwise reversible PNP reaction towards completion of digestion. Upon such phosphorylation, the ATP produced may be detected by any of the conventional detection means including, for example, the light-generating luciferase-catalyzed reaction with luciferin. Alternatively, the byproduct of the phosphorylation step (and especially pyruvate) may be determined by conventional means including, for example, the determination of pyruvate by the lactate dehydrogenase (LDH) catalyzed reaction with NADH. By monitoring the disappearance of NADH in such cases (either photometrically or by fluorescence), a value can be obtained which is functionally related to the ADP produced by the digestion step, and thus to the presence and amount of target nucleotide sequence in the nucleic acid (DNA) of the sample. Such detection steps are also described in more detail in U.S. applications Ser. No. 729,502 and 729,503.

Based on the above description of the method and reagent complex, various forms of reagent kits provided by the present invention will become apparent. Thus, for example the following elements are generally present in the reagent kit:
A. reagent complex,
B. digestion enzymes (with cofactors),
C. phosphorylation enzymes (with cofactors and coreactants),
D. detection systems.

In many forms of the invention, displacement aids such as polyethylene glycol (See U.S. application Ser. No. 684,308 of J. I. Williams et al, filed Dec. 20, 1984) or a recombination protein such as rec A protein from E. Coli (as described in the above-referenced U.S. application Ser. No. 684,305 of Collins et al) may be used; provided, however, that if an ATP-dependant enzyme (such as rec A protein) is used to enhance displacement, then any ATP (and byproducts) introduced as co-factors must be removed after displacement and before digestion or compensated for.

As described above, a cascade can be generated by initial ADP production (through digestion of a displaced strand), leading to ATP, rec A activation (with byproduct ADP rephosphorylated to ATP) and enhanced further displacement.

It is preferred that certain combinations of such ingredients be either packaged together; or, if packaged separately, they are preferably introduced together into the reaction mixture. Such combinations include especially the phosphorylation enzyme (with its cofactors) and the digestion enzyme (and especially polynucleotide phosphorylase). In the case where a digestion enzyme producing AMP is used (such as snake venom phosphodiesterase), then it is generally not necessary to package the phosphorylation enzymes with the digestion enzyme since the digestion enzyme will normally digest irreversably by itself. In such cases, however, it is preferred to package or introduce the two phosphorylation enzymes (with coreactants) together such that, for example, myokinase and pyruvate kinase are either packaged or introduced together, each with appropriate cofactors and coreactants, e.g., CTP and phosphoenolpyruvate, respectively.

It is further contemplated that, in some forms of the invention, enzymes such as ATPases, apyrase, phosphatases or pyrophosphatases may be present in one or more ingredients in extremely low concentrations for the purpose of converting any ATP which forms nonspecifically during enzyme storage to a form (and especially adenosine and inorganic phosphate) which will not provide an interfering signal during use. It is especially contemplated to include such enzymes in the phosphorylation enzymes and the detection system reagents (LKB includes such ATPase in a luciferase reagent for analogous reasons). Boronates and other nucleoside phosphate complexing agents may be used for the same purpose.

Figure 1B:
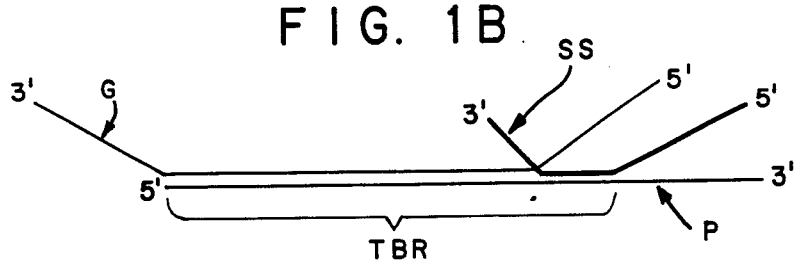
in FIG. 1B, an intermediate stage of the displacement step; and, in FIG. 1C, the digestion of displaced signal strand and phosphorylation of ADP to ATP.
Figure 1C:
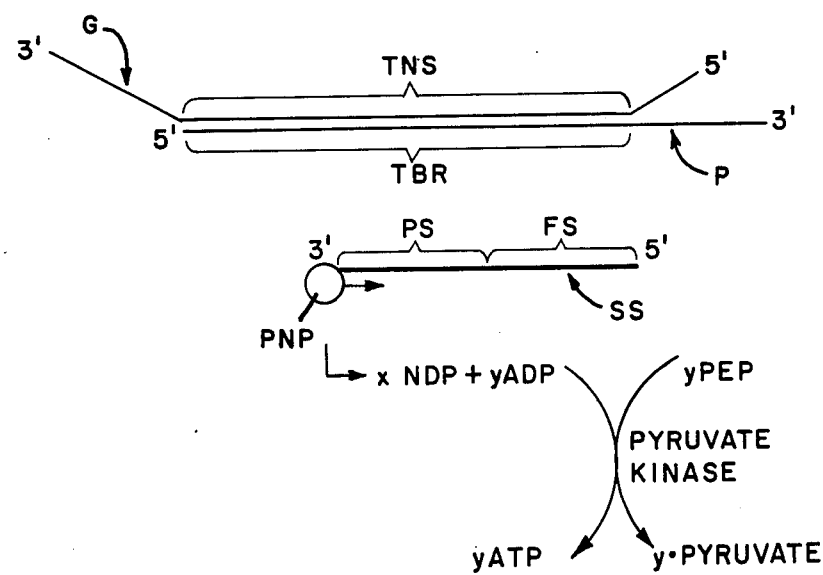
FIG. 1 is a schematic view, in three parts (FIGS. 1A, 1B and 1C) of a first embodiment of the present invention showing.

FIG. 1, comprising FIGS. 1A, 1B and 1C, illustrates a first embodiment of the present invention. In FIG. 1A, a reagent complex is shown containing a DNA probe polynucleotide P and a RNA signal strand polynucleotide SS. In this embodiment, the major portion of the probe polynucleotide P is the target binding region TBR complementary to the target nucleotide sequence to be analyzed. A portion, the initial binding region IBR, of the target binding region TBR is single-stranded in the reagent complex. The other portion, the signal-strand binding region LBR, of the target binding region TBR is bound by complementary base pairing to a segment, the pairing segment PS, of the signal strand SS. Looking at the signal strand SS, the pairing signal PS occupies the tail (portion nearest the 3' end) and a free segment FS occupies the head (segment nearest the 5' end). In use, such reagent complex is contacted with a sample which contains nucleic acid and especially sample DNA. When such a piece of sample DNA G containing the target nucleotide sequence contacts a reagent complex as shown in FIG. 1A, it can hybridize initially at the initial binding region IBR.

FIG. 1B illustrates an intermediate stage of the displacement of the signal strand SS from the target binding region TBR of the probe polynucleotide by the sample nucleic acid strand G. In this intermediate structure, the 3' end of the signal strand (actually a portion of the pairing segment PS) has been displaced from the probe polynucleotide, but the signal strand SS remains bound by complementary base pairing to the portion of the target binding region TBR nearest the 3' end of the probe polynucleotide. By mechanisms described in U.S. application Ser. No. 607,885, the structure shown in FIG. 1B of this application may be subjected to zippering and unzippering to the left and right until such point as the signal strand SS dissociates from the probe polynucleotide P. FIG. 1C illustrates the DNA/DNA hybrid between the target nucleotide sequence TNS of the sample nucleic acid strand G and the target binding region TBR of the probe polynucleotide P that forms after the completion of the displacement. The signal strand SS is now displaced and in solution in single-stranded form. Also as illustrated in FIG. 1C, the enzyme polynucleotide phosphorylase (PNP) can attach to the 3' end of the signal strand SS and digest such RNA signal strand processively from the 3' end. In this embodiment, the polynucleotide phosphorylase can digest processively through the pairing segment PS and then through the free segment FS of the signal strand SS. As illustrated in FIG. 1C, such digestion can release all of the ribonucleotides of the signal strand polynucleotide as nucleoside diphosphates, illustrated as x nucleoside diphosphates other than ADP (x NDP) and as y adenosine diphosphates (y ADP). Provided that a sufficient amount of pyruvate kinase and phosphoenolpyruvate are present, reaction will occur in which y molecules of PEP will react with y molecules of ADP (catalyzed by pyruvate kinase) so as to form y molecules of ATP and y molecules of pyruvate. In the present method, either the ATP so-produced or the pyruvate so-produced is detected. The amount so-detected will be functionally related to the number of signal strand polynucleotides SS displaced from reagent complexes, which will in turn be functionally related to the amount of target nucleotide sequences TNS present in the nucleic acid of the sample.

FIGS. 2A, 2B, 2C and 2D illustrate four additional embodiments of the reagent complex of the present invention, each of which, like the reagent complex shown in FIG. 1A, contains a DNA probe polynucleotide P and an RNA signal strand polynucleotide SS. In the embodiment shown in FIG. 2A, the signal strand polynucleotide contains a pairing segment PS which binds to a portion (the signal strand pairing region LBR) of the target binding region TBR of the probe polynucleotide P nearest the 5' end of the probe polynucleotide P. Accordingly, hybridization by a target nucleotide sequence will normally proceed first within the initial binding region IBR which is closer to the 3' end of the probe polynucleotide than the signal strand binding region LBR. Accordingly, the 3' end of the signal strand polynucleotide SS will be displaced only at the completion of the displacement event. Accordingly, no structure such as shown in FIG. 1B will form in which displacement has not been completed, but a free 3' end of the signal strand polynucleotide SS is in signal-stranded form and therefore is available for digestion. Comparing these two embodiments, the embodiment of FIG. 1 has the advantage that digestion may proceed during the displacement event and help drive the displacement toward completion. The embodiment of FIG. 2A has the advantage, however, that digestion will not occur because of sample nucleic acid strands which have part, but not the 3' end of, the target nucleotide sequence.

In the embodiment of reagent complex illustrated in FIG. 2B, being the type used in the Examples, the signal strand polynucleotide SS contains only nucleotides bound in the reagent complex to the signal strand binding region LBR of the probe polynucleotide P. Accordingly, this reagent complex may be used in combination with digestion enzymes which attack any single-stranded ribonucleotide segment (such as rat liver alkaline RNase I). In use, such reagent complex can hybridize with the target nucleotide sequence initially in the initial binding region IBR. Strand displacement through the signal strand binding region LBR would follow, resulting in dissociation of the signal strand polynucleotide SS from the probe polynucleotide P. Digestion and phosphorylation will proceed as illustrated in FIG. 1C if the digestion enzyme produces ribonucleotide diphosphates. In the event that the digestion enzyme produces ribonucleoside monophosphates, phosphorylation will normally then proceed in two steps, as described in U.S. application Ser. Nos. 729,502 and 729,503, referenced above, for forms where AMP is phosphorylated.

The reagent complex of a fourth embodiment, as illustrated in FIG. 2C, contains a signal strand polynucleotide SS whose nucleotides are totally bound to the signal strand binding region LBR of the target binding region TBR of the probe polynucleotide P. The signal strand binding region LBR is located, however, not at an end, but rather centrally within, the target binding region TBR. Accordingly, two initial binding regions IBR-1 and IBR-2 are present within the probe polynucleotide. Accordingly, hybridization by the target nucleotide sequence may proceed initially within either IBR-1 or IBR-2, followed eventually by displacement of the signal strand polynucleotide SS from the signal strand binding region LBR. Displacement in such cases has been demonstrated experimentally in Example 4 of application Ser. No. 684,305 and the potential mechanisms are described in relationship to FIG. 1F of U.S. application Ser. No. 607,885. Upon displacement, the signal strand polynucleotide SS of FIG. 2C would be subjected to digestion and phosphorylation followed by detection in similar matter to the previous embodiments.

FIG. 2D illustrates a reagent complex similar to that of FIG. 2B in that the DNA probe P contains a target binding region TBR complementary to the target nucleotide sequence to be determined. The 3' end of segment TBR is an initial binding region IBR in single-stranded form so as to promote nucleation by the target nucleotide sequence, as in FIG. 2B.

The signal strand binding region (LBR) of the probe P in FIG. 2D has bound thereto by complementary base pairing a series of signal strands, illustrated as signal strands SS-1, SS-2, SS-3, SS-4 and SS-5. In practice, such multiple signal strands may be formed by treating the reagent complex of FIG. 2B lightly (for a short time and at low enzyme concentrations) with RNase H, which will cut signal strand SS of FIG. 2B randomly, generating fragments SS-1, SS-2, SS-3, SS-4 and SS-5. It may be desirable to remove any fragments too loosely bound to probe strand P by chromatography before use. While the fragments SS-1 through SS-5, as illustrated in FIG. 2D, are all fully-bound, reagent complexes with some segments bound only at then 3'-terminal segments can also be generated, e.g., by light RNase H digestion of the reagent complex of FIGS. 1A or 2A.

In use, when the reagent complex of FIG. 2D is contacted by target nucleotide sequence, a DNA/DNA hybrid can form, first in the intial binding region IBR, and then progressively through the signal strand binding region LBR. As the DNA/DNA double helix forms in LBR, signal strand SS-5, then SS-4, then SS-3, then SS-2 and finally SSS-1 will be displaced. In subsequent steps, each can be digested to nucleoside phosphates (including ADP or AMP) and the AMP or ADP phosphorylated as described above.

FIG. 3A illustrates a sixth embodiment of the reagent complex of the present invention, wherein the probe polynucleotide and signal strand polynucleotide are part of a continous RNA polynucleotide strand. Proceeding from the 5' end of this strand, there is illustrated a target binding region TBR complementary to the DNA target nucleotide sequence to be detected, an intermediate segment IS and a pairing segment PS at the 3' end. Because the pairing segment PS is complementary to (in the sense of an inverted repeat) a portion (the signal strand pairing segment LBR) of the target binding region TBR, it forms in the reagent complex a RNA/RNA double-stranded portion. The other portion (the initial binding region IBR) of the target binding region (illustrated in this embodiment as the 5' end of the target binding region TBR) is in single-stranded form. Manufacture of such a reagent complex is described in U.S. application Ser. No. 729,504 of E. F. Fritsch and M. Collins, filed May 2, 1985 and assigned to Genetics Institute, Inc.

Upon contact with a sample DNA nucleic acid strand G having the appropriate target nucleotide sequence TNS, the reagent complex of FIG. 3A will undergo nucleation and strand displacement in a manner analagous to that described above in relation to FIGS. 1B and 1C. At the completion of strand displacement, the intermediate structure shown in FIG. 3B will be formed. In this structure, the target binding region TBR of the continuous RNA strand will be bound in a RNA/DNA duplex to the target nucleotide sequence TNS of the sample DNA polynucleotide strand G. The remainder of the RNA polynucleotide, containing the intermediate segment IS and the pairing segment PS, will be attached to this duplex, but will be in single-stranded form. A processive digestion enzyme (polynucleotide phosphorylase PNP) can now attach to the free 3' end of the RNA strand (the 3' end of the pairing segment PS) and digest through the pairing segment PS and the intermediate segment IS. Upon completion of this digestion, m nucleoside diphosphates other than ADP (mNDP) and n adenosine diphosphates (nADP) will have been generated as shown in FIG. 3C. The remaining undigested portion of the probe polynucleotides would include the target binding region TBR (which is a ribonucleotide segment) bound to the target nucleotide sequence TNS of the sample strand G (which is a deoxyribonucleotide segment).

In some forms of the invention, one now phosphorylates and detects solely the nADP molecules formed by this digestion of the pairing segment PS and the intermediate segment IS. In other forms of the invention, however, ribonuclease H (RNase H) is present or added at this point and will selectively digest the RNA of RNA/DNA double helices. This is indicated graphically by the arrows pointing at the target binding region TBR in FIG. 3C. FIG. 3D illustrates the RNA oligonucleotides which could form by the action of RNAse H on the target binding region TBR, each of which is short enough to dissociate in single-stranded form and can be digested by polynucleotide phosphorylase PNP as shown in FIG. 3D to generate p molecules of nucleoside diphosphates other than ADP (p NDP) and q molecules of adenosine diphosphate (q ADP).

FIG. 3E illustrates the phosphorylation of the adenosine diphosphates formed both from the digestion shown in FIG. 3C (nADP) and from the digestion shown in FIG. 3D (q ADP). With sufficient pyruvate kinase and phosphoenol pyruvate (PEP), (n+q) PEPs and (n+q) ADPs are consumed, and (n +q) pyruvate molecules and (n+q) ATP molecules are produced. Either of these products can be detected.

Furthermore, the sample strand G can now hybridize to a second reagent complex molecule.

In connection with FIG. 2D, above, a reagent complex was described with multiple signal strands SS-1 thru SS-5, formed, for example, by digestion of the ssignal strand SS of FIG. 2B with RNase H (which is specific for the RNA strand of DNA/RNA double helices). As indicated in the text, enzymes may also be used to digest RNA/DNA double helices which may form in the signal strand SS or pairing segment PS after displacement, but with embodiments such as FIGS. 1A, 2A, 2B, 2C and 2D employing DNA probe polynucleotides. An exemplary enzyme used here (especially as an auxiliary digestion enzyme) is cobra venom RNAse.

FIG. 4A illustrates a seventh embodiment of the invention wherein the probe polynucleotide P and the signal strand SS are each RNA. The pairing segment PS contains the 3' terminus of the signal strand SS. The signal strand binding region LBR contains the 3' terminus of the probe polynucleotide P. Since pairing segment PS is bound by complementary base pairing to signal strand binding region LBR, both strands are protected from attack by a solely-processive digestion enzyme. The single-stranded segments FS and TBR contain no free 3' termini.

Upon displacement and digestion with PNP, the entire signal strand SS will be digested as in previous embodiments. The RNA probe polynucleotide P will, at this stage be bound to sample DNA bearing the target nucleotide sequence TNS. Further digestion by RNAse H and then PNP, in the manner described in relation to FIGS. 3C and 3D, may proceed now, producing additional ADP. Detection of the ADP may proceed in this embodiment as with the earlier-described embodiments.

The present invention is further illustrated by the following Examples:

EXAMPLE 1

Preparation of RNA Signal Strands

A synthetic RNA of length 52 nucleotides was constructed as follows. 10 $\mu$g of pSp64 DNA was linearized by restriction with Eco R1 endonuclease. This DNA was extracted once with a mixture of phenol, chloroform and isoamylalcohol (25:24:1). Following separation of the aqueous and organic phases and reextraction of the organic phase with an equal volume of 0.2M NaCl buffered with TE (10 mM Tris HCl, pH 8.0; 1 mM EDTA), the pooled aqueous phases were extracted 3 times with water saturated diethyl ether and the DNA precipitated by addition of ethyl alcohol to 75% (v/v). RNA was prepared from this template as follows. Each reaction mixture (components from Promega Biotech) contains 40 mM Tris HCl (pH 7.5), 6 mM $MgCl_2$, 2 mM spermidine, 10 mM NaCl, 10 mM dithiothreitol, 500 $\mu$M of each of the four rNTPs, 60 units of RNAsin, 10-50 mCi [$\alpha^{32}$P] rATP and 2 mg of EcoRI linearized pSp64 DNA. The reaction was initiated by the addition of 45 units of SP6 polymerase in a final volume of 50 μl. Following incubation for 60 minutes at 37° C., an additional 60 units of RNAsin and 2 units of DNase 1 were added and incubation continued for an additional 15 minutes at 37° C. Following adjustment of the salt concentration to 400 mM with 4M NaCl, the reaction was extracted as described above for linearized DNA. Nucleotides were quantitatively removed by centrifugation of the phenolchloroform -isoamyl alcohol extracted aqueous phase over a 1.5 ml Sephadex G-50 spin column. Removal of nucleotides was greater than 99.5% as judged by polyethyleneimine cellulose chromatography of the G-50 fractions followed by Cerenkov counting of the $\alpha[^{32}P]$ ATP.

Preparation of RNA-DNA Hybrid

A given RNA preparation was titrated with varying amounts of complementary "probe" DNA to determine the ratio of input DNA and RNA required to obtain 90-95% incorporation of the radioactivity as RNA into hybrid as judged by agarose gel electrophoresis. A constant amount of 52-mer RNA was hybridized to several concentrations (0.01–0.1 μg/ul) of M13mp11 single stranded circular DNA in the presence of 0.2 M NaCl and TE buffer. Following incubation of therreaction for 30 minutes at 65° C. the reaction was slow-cooled and the degree of hybridization quantitated by agarose gel electrophesis followed by cutting and counting of the free 52-mer and hybrid bands.

Displacement Reaction 52-mer:M13mpll hybrid (reagent complex) was incubated for 120 minutes at 65° C. in a final volume of 10 μl and in the presence or absence of an equal mass of M13mp11 competitor DNA relative to probe M13mp10 DNA. Since the probe and competitor DNA's are of equal molecular weight, this reaction constituted approximately a 1:1 ratio of competitor to 52-mer labeled probe strand.

Conversion of Displaced RNA to Nucleoside Phosphates

Following displacement, the reaction was diluted to 0.1M NaCl with distilled deionized DEPC (diethylpyrocarbonate) treated water and an equal volume of 2X phosphorolysis kinase reaction mixture was added. This resulted in a final concentration of copponents of 50 mM NaCl, 100 mM Tris HCl (pH 8.5), 1 mm 2-mercaptoethanol, 10 mM $MgCl_2$, 10 mM orthophosphate, 20 mM phophoenol pyruvate, 0.02 units of polynucleotide phosphorylase, and 1 unit of pyruvate kinase. Following incubation of the reaction for 60 minutes at 50° C., the amount of ATP, ADP and incompletely digested plus intact RNA was quantitated by polyethyleneimine cellulose chromatography. The results of one such displacement and conversion reaction are shown in Table 1.

TABLE 1

| Displacement of 52 mer RNA hybrids Conversion to ATP | | | | |
|---|---|---|---|---|
| | Hybrid + lamba DNA[1] (1:1) | | Hybrid + Competitor DNA[2] (1:1) | |
| Post displacement time of conversion (min) % Total CPM[3] as: | 0 | 60 | 0 | 60 |

TABLE 1-continued

| Displacement of 52 mer RNA hybrids Conversion to ATP | | | | |
|---|---|---|---|---|
| | Hybrid + lamba DNA[1] (1:1) | | Hybrid + Competitor DNA[2] (1:1) | |
| ATP | 0.4 | 0.5 | 0.6 | 89.4 |
| ADP | 0.5 | 0.03 | 0.2 | 6.3 |
| RNA | 99.1 | 99.4 | 99.2 | 4.3 |

[1]Lamda DNA was used as control noncompetitor DNA.
[2]Probe strand of hybrid is M13mp11 DNA, competitor is M13mp10 DNA.
[3]Assayed by polyethylenimine cellulose chromatograpy.

EXAMPLE 2

Preparation of RNA

The preparation of a 23-mer RNA was conducted as described above with the following exceptions. The template pSp64 DNA was linearized with Hinc II restriction endonuclease. The 23-mer RNA was purified from contaminating $\alpha[^{32}P]$ ATP and other nucleotides by centrifugation of the post phenol extract reaction mixture through a 1.5 ml Bio Gel P-6 spin column.

Preparation of Hybrid

Hybrid was prepared at the level of 93% incorporation of total RNA into M13mp11 probe containing hybrid by procedures described above in Example 1.

Displacement Reaction 23-mer RNA:M13mp11 hybrids (reagent complexes) were used to detect competitor M13mp10 DNA as described in Example 1, except that the displacement reaction was conducted at 50° C. for 1 hour. A different M13mp10 preparation used was less effective on a mass basis at displacement of the 23-mer hybrid as well as the 52-mer hybrid (not shown).

Conversion of Displaced RNA to Nucleoside Phosphates

Conversion reactions using pyruvate kinase and polynucleotide phosphorylase were conducted as described in Example 1. The results of one such experiment at relative levels of 0.6 and 1 mole of competitor per mole of hybrid probe strands are shown in Table 2.

TABLE 2

| Competitor/hybrid[1] | 0.0 | 0.6 | 1.0 |
|---|---|---|---|
| % Total cpm as free RNA[2] | 22.3 | 29.6 | 43.8 |
| % Total cpm converted[3]: | | | |
| ATP | 17.6 | 23.2 | 38.8 |
| ADP | 3.2 | 6.6 | 7.8 |
| % Total cpm unconverted[4] | 79.2 | 70.2 | 53.4 |

[1]Values represent relative amounts only. Competitor is DNA M13mp10, probe strand is M13mp11.
[2]Assayed by agarose gel electrophoresis
[3]Assayed by polyethyleneimine cellulose chromatography.
[4]Hybridized RNA and oligoribonucleotides of length 3 or greater.

EXAMPLE 3

Preparation of RNA

Preparation of a 195 nucleotide RNA was accomplished as follows. A 375BP EcoRI BamHI fragment from PBR-322 was subcloned into pSp65 DNA following linearization of the latter with EcoRI and BamHI restriction endonucleases. Following linearization of the derivative pSp65-15 DNA with EcoRV, a 195 long RNA was prepared by transcription of the pSp65-15 template in the presence of all four nucleoside triphosphates including α[$^{32}$P] ATP. Following transcription, the RNA was freed of nucleoside triphosphates by Sephadex G-50 gel filtration.

Preparation of Hybrid

Hybrid was prepared to the level of 90% incorporation ofuuniformly [$^{32}$P] adenosine-labeled RNA into single stranded M13mp8-20-C DNA hybrids by procedure described above in Example 1.

Displacement Reaction

Displacement reactions were conducted in the buffer system used for the polynucleotide phosphorylase/pyruvate kinase reactions minus the enzymes. Displacement and conversion of the RNA to signal molecule ADP and ATP are routinely conducted simultaneously and in the same solution. For the purpose of this Example, separation of the displacement and conversion steps facilitates quantitation of individual displacement andc-conversion steps. This reaction mixture contained, in addition to the components listed in Example 1, approximately 0.5 pmole of 195-mer hybrid with M13mp 8-20 DNA (reagent complex), 0-7 mg of M13mp19 3/2 competitor or equivalent masses of M13mp11 noncompetitor DNA in a final volume of 20 μl. The latter DNA is identical to the competitor DNA except that it does not contain the 1.1 kbase insert complimentary to the region of M13mp8-20 which binds the 195-mer RNA. Two sets of reactions were conducted at 0 or 0.10 M added NaCl toevaluate the effect of ionic strength on the displacement and subsequent conversion and detection of analyte and control (non competitor) DNA's. Following incubation of the displacement reaction mixture for 30 minutes at 65° C., the samples were removed to room temperature and 4 ul of each reaction representing various amounts of input competitor or control DNA were assayed for extent of displacement by electrophoresis on a 1.5% agarose gel. To each reaction mixture was then added 12 μl of 1×PNP/PK buffer containing approximately 0.028 units of polynucleotide phosphorylase and 0.4 units of pyruvate kinase. Following incubation of this reaction mixture for 30 minutes at 50° C., 4 μl of each reaction mixture were applied to PEI cellulose. Following chromatography of the sample in 0.8M LiCl and 0.8M acetic acid, spots corresponding to RNA, ATP and ADP were cut out and quantitated by Cerenkov counting. The remainder of each reaction mixtures was adjusted to a final volume of 250 μl with distilled deionized water and the ATP quantitated by bioulmenescence in an LKB 1250 luminometer using standard reagents. The results of these analyses are presented in Tables 3 and 4. The 9.8% value of free RNA in Table 4 is attributable to the proportion unhybridized (note the 90% hybridization efficiency stated above).

TABLE 3

Displacement, Conversion and Detection, Standard Buffer

| No. | Competitor DNA (ug) | % Total RNA[1] displaced | % Total cpm as:[2] | | | Biolumenescence |
|---|---|---|---|---|---|---|
| | | | RNA | ADP | ATP | |
| 1 | 0 | 11.5 | 94.1 | 0.8 | 0.5 | 37720 |
| 2 | 1.78 | 41.8 | 62.8 | 7.8 | 29.4 | 150900 |
| 3 | 3.56 | 72.3 | 48.5 | 10.8 | 40.6 | 243800 |
| 4 | 5.34 | 84.8 | 54.8 | 12.1 | 33.2 | 345600 |
| 5 | 7.12 | 86.9 | 46.1 | 6.1 | 47.9 | 452700 |

TABLE 4

Displacement, Conversion and Detection Buffer + 0.1 M NaCl

| No. | Competitor DNA (ug) | % Total RNA[1] free | % Total cpm as:[2] | | | Biolumenescence |
|---|---|---|---|---|---|---|
| | | | RNA | ADP | ATP | |
| 1 | 0 | 9.8 | 94.0 | 3.0 | 3.0 | 23620 |
| 2 | 1.78 | 60.2 | 67.3 | 6.9 | 25.8 | 75340 |
| 3 | 3.56 | 76.8 | 54.9 | 10.1 | 35.0 | 140800 |
| 4 | 5.34 | 84.4 | 65.7 | 6.0 | 28.3 | 187800 |
| 5 | 7.12 | 88.1 | 49.6 | 10.1 | 40.4 | 355200 |

[1] Analyzed by Agarose gel electrophoresis
[2] Analyzed by polythyleneimine cellulose chromatography

What is claimed is:

1. A method for determining the presence of a predetermined target nucleotide sequence in the DNA of a biological sample which comprises the steps:
   (a) providing a reagent complex of (i) a probe polynucleotide which is capable of base pair binding via hydrogen bonds of purine/pyrimidine bases to the DNA target nucleotide sequence, and (ii) an RNA signal strand polynucleotide which is bound by base pair binding via hydrogen bonds of purine/pyrimidine base pairs to the probe polynucleotide in a region of the probe polynucleotide at least partially coextensive with the region in which the probe polynucleotide is capable of binding to the DNA target nucleotide sequence;
   (b) contacting the reagent complex with a sample under conditions in which the DNA target nucleotide sequence, if present, binds to the probe polynucleotide and displaces the RNA signal strand polynucleotide from the reagent complex;
   (c) without separation, digesting the displaced RNA signal strand polynucleotide selectively with respect to RNA signal strand polynucleotide remaining in reagent complex; and
   (d) detecting the presence of the digestion products of digesting the displaced RNA signal strand polynucleotide.

2. The method of claim 1 wherein the detecting step (d) comprises providing an enzymatic reaction system which produces a detectable enzymatic reaction product in an amount functionally related to the presence and amount of adenosine phosphates produced in the digesting step (c).

3. The method of claim 2 wherein the contacting step (b), the digesting step (c) and the detecting step (d) are all conducted in solution.

4. The method of claim 3 wherein said steps are conducted in solution without an intervening separation.

5. The method of claim 2 wherein:
   the 3'-terminal nucleotide of the RNA signal strand polynucleotide is bound in the reagent complex to a nucleotide of the probe polynucleotide and the probe polynucleotide does not contain an unbound 3'-terminal ribonucleotide; and
   the digesting step (c) comprises digesting ribopolynucleotides processively from a single-stranded 3'-terminus.

6. The method of claim 5 wherein the 3'-terminal nucleotide of the probe polynucleotide is a deoxyribonucleotide.

7. The method of claim 6 wherein the probe polynucleotide is DNA.

8. The method of claim 5 wherein the 3'-terminal nucleotide of the probe polynucleotide is a ribonucleotide and is bound in the reagent complex to a nucleotide of the RNA signal strand polynucleotide.

9. The method of claim 5 wherein the digesting step (c) comprises digesting ribonucleotides processively from a single-stranded 3'-terminus with a polynucleotide phosphorylase and inorganic phosphate to produce ribonucleoside diphosphatss, and the detecting step (d) comprises phosphorylating the adenosine diphosphate (ADP) among the ribonucleotide diphosphates to adenosine triphosphate (ATP).

10. The method of claim 9 wherein the phosphorylating ADP step employs an excess of an organophosphate compound and employs a kinase enzyme effective to catalyze the production of ATP from ADP and the organophosphate compound.

11. The method of claim 10 wherein the organophosphate compound is phosphoenol pyruvate and the kinase enzyme is pyruvate kinase.

12. The method of claim 10 wherein the excess organophosphate compound and the kinase enzyme are present in the reaction mixture during the digesting step (c), whereby the digesting step (c) is driven toward completion by the phosphorylating ADP step.

13. The method of claim 1 wherein the double helix between signal strand polynucleotide and probe polynucleotide is a DNA/RNA double helical segment and the digesting step (c) employs a first digestion enzyme which digests single-stranded polyribonucleotide segments to ribonucleoside phosphates and a second digestion enzyme which selective cleaves phosphodiester linkages of RNA/RNA double helical segments to produce 3' hydroxyl ends.

14. The method of claim 13 wherein the first digestion enzyme is polynucleotide phosphorylase.

15. The method of claim 14 wherein the second digestion enzyme is cobra venom ribonuclease.

16. The method of claim 1 wherein the probe polynucleotide and signal strand are both RNA.

17. The method of claim 16 wherein the 3' end of the signal strand is bound to the probe polynucleotide by complementary base pairing.

18. The method of claim 17 wherein the 5' end of the pairing region of the signal strand polynucleotide is linked by phosphate/sugar backbone to the 3' end of the portion of the probe polynucleotide capable of binding to the target nucleotide sequence.

19. A kit for determining the presence of a predetermined target nucleotide sequence in hhe DNA of a biological sample which comprises:
 (a) a reagent complex of (i) a probe polynucleotide which is capable of base pair binding via hydrogen bonds of purine/pyrimidine bases to the DNA target nucleotide sequence, and (ii) an RNA signal strand polynucleotide which is bound by base pair binding via hydrogen bonds of purine/pyrimidine base pairs to the probe polynucleotide in a region of the probe polynucleotide at least partially coextensive with the region in which the probe polynucleotide is capable of binding to the DNA target nucleotide sequence; the 3'-terminal nucleotide of the RNA signal strand polynucleotide being bound in the reagent complex to a nucleotide of the probe polynucleotide; and the probe polynucleotide not containing an unbound 3'-terminal ribonucleotide having a 3' hydroxyl;
 (b) a digestion enzyme specific for 3'-terminal ribonucleotides which are in single-stranded form;
 (c) reactants and enzymes effective to convert adenosine phosphates produced by the digestion enzyme to ATP, and
 (d) means for detecting ATP or a byproduct of the conversion of adenosine phosphates to ATP.

20. The kit of claim 19 wherein the digestion enzyme is polynucleotide phosphorylase and the kit further comprises inorganic phosphates, whereby the adenosine phosphates produced by the digestion enzyme are nucleoside diphosphates.

21. The kit of claim 20 wherein the reactants and enzymes (c) comprise an excess of an organophosphate compound and a kinase enzyme effective to produce ATP from the organophosphate compound and ADP.

22. The kit of claim 21 wherein the polynucleotide phosphorylase, the organophosphate compound and the kinase enzyme are packaged together.

23. The kit of claim 21 wherein the kinase enzyme is pyruvate kinase.

24. The kit of claim 21 wherein the kinase enzyme is creatine kinase.

25. The kit of claim 19 wherein the probe polynucleotide is RNA.

26. The kit of claim 19 wherein the probe polynucleotide is DNA.

27. The kit of claim 26 further comprising a second digestion enzyme specific for ribonucleotide phosphodiester bonds in an RNA/RNA double helical segments.

28. A reagent complex comprising:
 (i) a probe polynucleotide which is capable of base pair binding via hydrogen bonds of purine/pyrimidine bases to the DNA target nucleotide sequence, and
 (ii) an RNA signal strand polynucleotide which is bound by base pair binding via hydrogen bonds of purine/pyrimidine base pairs to the probe polynucleotide in a region of the probe polynucleotide at least partially coextensive with the region in which the probe polynucleotide is capable of binding to the DNA target nucleotide sequence;
 the 3'-terminal nucleotide of the RNA signal strand polynucleotide being bound in the reagent complex to a nucleotide of the probe polynucleoide; and
 the probe polynucleotide not containing an unbound 3'-terminal ribonucleotide having a 3' hydroxyl.

29. The reagent complex of claim 28 wherein the probe polynucleotide is DNA.

30. The reagent complex of claim 28 wherein the probe polynucleotide is RNA.

31. The reagent complex of claim 30 wherein the 5' end of the pairing region of the signal strand polynucleotide is linked by phosphate/sugar backbone to the 3' end of the portion of the probe polynucleotide capable of binding to the target nucleotide segment.

* * * * *